United States Patent
Ignatiev et al.

(10) Patent No.: US 6,410,190 B1
(45) Date of Patent: Jun. 25, 2002

(54) PROCESS FOR THE PURIFICATION OF METHANIDE ELECTROLYTES

(75) Inventors: Nikolai Ignatiev, Duisburg; Peter Sartori, Rheinberg; Peter Barthen, Duisburg, all of (DE)

(73) Assignee: Merck Patent Gesellschaft mit beschraenkter Haftung (DE)

(*) Notice: Subject to any disclaimer, the term of this patent is extended or adjusted under 35 U.S.C. 154(b) by 0 days.

(21) Appl. No.: 09/560,137

(22) Filed: Apr. 28, 2000

(30) Foreign Application Priority Data

Apr. 28, 1999 (DE) .......................... 199 19 346

(51) Int. Cl.⁷ ............................... H01M 6/14
(52) U.S. Cl. ..................... 429/347; 522/25; 560/14
(58) Field of Search .................. 522/25; 429/347; 560/14

(56) References Cited

U.S. PATENT DOCUMENTS

| | | | | |
|---|---|---|---|---|
| 5,273,840 A | * | 12/1993 | Dominey | 429/192 |
| 5,389,467 A | * | 2/1995 | Herr et al. | 429/194 |
| 5,554,664 A | * | 9/1996 | Lamanna et al. | 522/25 |
| 6,046,368 A | * | 4/2000 | Lamanna et al. | 568/683 |

OTHER PUBLICATIONS

Turowsky et al., "Tris(trifluoromethyl)sulfonyl)methane, $HC(SO_2CF_3)_3$", Inorganic Chemistry, vol. 27, No. 12, 1988, pp. 2135–2137.*

* cited by examiner

*Primary Examiner*—Carol Chaney
(74) *Attorney, Agent, or Firm*—Millen, White, Zelano & Branigan, P.C.

(57) ABSTRACT

The invention relates to a process for the preparation of organic methanide electrolytes in useable quality for use in electrochemical cells and batteries.

20 Claims, No Drawings

PROCESS FOR THE PURIFICATION OF METHANIDE ELECTROLYTES

SUMMARY OF THE INVENTION

The invention relates to a process for the preparation of organic methanide electrolytes in useable quality for use in electrochemical cells.

The tris(perfluoroalkanesulfonyl)methanide class of compounds was described for the first time by Turowsky et al. in Inorgan. Chem., 1988, 27, 2135–2137 with reference to tris(trifluoromethanesulfonyl)methane. This C—H acidic compound reacts with bases to give the corresponding salts. The anion is planar, and the negative charge can be delocalized very well by the strongly electron-withdrawing substituents.

The lithium salt lithium tris(trifluoromethanesulfonyl)-methanide has been investigated for some time with respect to its suitability as conductive salt in secondary batteries owing to its high conductivity and good solubility in aprotic solvents. Further advantages of this salt are its high electrochemical and thermal stability.

There are two processes for the preparation of such compounds. According to Turowsky et al., tris[trifluoromethanesulfonyl]methane is prepared by a Grignard reaction with trifluoromethanesulfonyl fluoride.

A two-step process as described by Koshar et al. in J. Org. Chem., 1973, 38, 3358–3363, and Benrabah et al. in J. Chem. Soc. Faraday Trans., 1993, 89(2), 355–359, likewise gives tris[trifluoromethanesulfonyl]methane.

Both processes give products which require purification for use as conductive salt. Purification methods used hitherto, which are based on reaction of the solvated salt with activated carbon and recrystallization, give products having a purity of, in general, not greater than 99.5% which still contain interfering contamination by water and foreign ions.

However, salts of this quality are not suitable for use in organic electrolytes.

DETAILED DESCRIPTION

An object of the present invention is therefore to provide an inexpensive, easy-to-perform process by means of which organic methanide electrolytes are obtained in high-purity form, making the products prepared suitable for use in battery electrolytes. For the purposes of the invention, "high-purity" is taken to mean degrees of purity of greater than 99.5%, e.g. 99.6, 99.7, 99.8, 99.9%, or greater.

One object according to the invention is achieved by a process for the preparation of high-purity methanides of the formula $$MC(SO_2(C_xF_{2x+1}))_3 \quad (I)$$

in which
x is 1, 2, 3, 4, 5, 6, 7 or 8, and
M is H, Li, Na, K, Rb, Cs, $Mg_{1/2}$, $Ca_{1/2}$, $Sr_{1/2}$ or $Ba_{1/2}$, which are suitable as electrolytes, by purification, characterized in that it comprises the following steps:
(i) reaction of a methanide of the formula (I) with concentrated sulfuric acid, and fractional rectification of the resultant free acid of said methanide,
(ii) reaction of the product of the formula (I) in which M=H obtained from (i) with phosphorus pentoxide at or above the melting point followed by fractional rectification,
(iii) taking-up of the product of the formula (I) in which M=H from (ii) in an aprotic organic solvent, and reaction with metallic Li, Na, K, Rb, Cs, Mg, Ca, Sr or Ba, or chlorides or hydrides thereof, or with alkyllithium, to give the corresponding metal methanides of the formula (I), and, if necessary, removal of excess reagent.

The process according to the invention gives materials having a purity of greater than 99.5%, preferably from 99.6% to 99.9%, which are thus suitable for use as electrolytes in batteries.

Surprisingly, it has been found that the reaction with concentrated sulfuric acid stabilizes the starting material and thus enables it to be distilled without decomposition. In addition, the addition of equivalent amounts or an excess of concentrated sulfuric acid enables the free acid $HC(SO_2CF_3)_3$ to be obtained directly from its salts and purified.

The addition, in accordance with the invention, of highly hygroscopic sulfuric acid already achieves a good drying effect, which can be increased further by addition of sulfur trioxide, corresponding to the water content of the crude product.

It has also been found that the fractional rectification of the pure fraction with addition of phosphorus pentoxide gives a pure product having a water content of from 5 to 30 ppm, preferably from 10 to 20 ppm. This highly effective drying can be carried out economically on amounts of any desired size.

The use in accordance with the invention of a solvent which is used exclusively or proportionately in the finished electrolyte is particularly advantageous. This makes isolation of the salt, which is complex, unnecessary.

In the reaction in process step (iii), gaseous hydrogen, hydrogen chloride or alkanes form as easily removable by-products. In this reaction, it was noted that the neutralization of $HC(SO_2CF_3)_3$ in accordance with the invention prevents decomposition phenomena at the anion, as has been observed in conventional processes.

The reduction of the volume of the electrolyte by distillation in accordance with the invention has the significant advantage that the large excess of desired oxygen nucleophile present in the solution displaces undesired nucleophiles from the coordination sphere of the lithium. This effect allows impurities to be removed by distillation. A highly concentrated electrolyte is obtained, which enables low storage and transport costs.

It has been found that the dilution of the highly concentrated electrolytes can be carried out with any desired solvents. It is therefore possible, in a simple manner, to employ the optimum solvent mixture and to provide electrolytes in any desired concentration.

The purification essentially consists of 3 process steps, which can preferably be followed by two further steps.

Any conventional source of methanide is suitable for the purification, including, e.g. methanide produced by the process of Turowsky et al. or Koshar et al, cited above.

1st Step

A methanide of the formula (I) having a purity of from 90% to 99.5% is introduced in batches into concentrated sulfuric acid (96–98% sulfuric acid), and the mixture is stirred at temperatures of from 10 to 40° C. The mixture is preferably reacted with freshly distilled sulfuric acid at temperatures of from 20 to 30° C. The sulfuric acid is added in equivalent amounts or in excess. The rectification apparatus with isothermal column is baked out under a protective-gas atmosphere. The distillation bridge must be heatable by means of heating tapes or the like. This keeps the distillation bridge at a constant temperature above the respective melting point. Fractional rectification is carried out in this apparatus.

2nd Step

The pure fraction from step 1 is mixed with phosphorus pentoxide in a distillation apparatus which has been baked out under a protective-gas atmosphere. The mixture is stirred for from 15 minutes to 5 hours at temperatures at or above the melting point of the acid. The reaction is preferably carried out for from 30 minutes to 90 minutes. The mixture is subsequently subjected to fractional rectification under reduced pressure.

The fractional rectification of the pure fraction from step 1 with addition of phosphorus pentoxide gives a pure product having a water content of, preferably, from 10 to 30 ppm.

3rd Step

The product from step 2 is dissolved in polar organic solvents under a dry inert-gas atmosphere. Aprotic solvents, such as DMC, DEC, EC, PC, BC, VC, cyclopentanone, sulfolane, DMS, 3-methyl-1,3-oxazolidin-2-one, ?-butyrolactone, EMC, MPC, BMC, EPC, BEC, DPC, 1,2-diethoxymethane, THF, 2-methyltetrahydrofuran, 1,3-dioxolane, methyl acetate, ethyl acetate, and mixtures thereof, are particularly suitable. The solution is mixed with lithium hydride, with metallic lithium (Li), with lithium chloride, in situ using a lithium positive electrode, or with alkyllithium. In order to prepare the sodium, potassium, rubidium, cesium, magnesium, calcium, strontium or barium compounds, a reaction can be carried out with metallic sodium (Na), potassium (K), rubidium (Rb), cesium (Cs), magnesium (Mg), calcium (Ca), strontium (Sr) or barium (Ba), sodium chloride, potassium chloride, rubidium chloride, cesium chloride, magnesium chloride, calcium chloride, strontium chloride, barium chloride, sodium hydride, potassium hydride, rubidium hydride, cesium hydride, magnesium hydride, calcium hydride, strontium hydride, or barium hydride. The mixture is stirred at temperatures of from 10° C. to 200° C. for from 10 minutes to 24 hours. The reaction is preferably carried out at temperatures of from 20° C. to 100° C. for from 25 minutes to 5 hours. The excess alkali metal reagent or alkaline earth metal reagent is subsequently filtered off.

4th Step

The volume of the solution from step 3 is, if necessary, reduced to $2/3$ to $1/4$. The solvent is preferably reduced to $1/3$. The distillation is carried out at atmospheric pressure at the boiling point of the corresponding solvent. The distillation can also be carried out under reduced pressure. The boiling points shift correspondingly.

5th Step

The high-viscosity electrolyte can be diluted to any desired extent with any desired solvents and solvent mixtures. Suitable solvents and solvent mixtures are all those employed in electrochemical storage media. The composition of the electrolyte can thus be matched in accordance with the specific requirements.

The inexpensive process which can be carried out using simple reagents and apparatuses gives products in good yields in a quality which is suitable for use in batteries. No explosive or toxic by-products are formed in this process.

The methanides can also be employed in proportions of from 1 to 99% in combination with other conductive salts which are used in electrochemical cells. Examples of suitable conductive salts are those selected from the group consisting of $LiPF_6$, $LiBF_4$, $LiClO_4$, $LiAsF_6$, $LiCF_3SO_3$, $LiN(CF_3SO_2)_2$ and $LiC(CF_3SO_2)_3$, and mixtures thereof. The electrolytes can also contain organic isocyanates (DE 199 44 603) for reducing the water content. The electrolytes may also contain organic alkali metal salts (DE 199 10 968) as additive. Suitable alkali metal salts are alkali metal borates of the general formula $$Li^+B^-(OR^1)_m(OR^2)_p$$

in which m and p are 0, 1, 2, 3 or 4, where m+p=4, and $R^1$ and $R^2$ are identical or different, are optionally bonded directly to one another via a single or double bond, are each, individually or together, an aromatic or aliphatic carboxylic, dicarboxylic or sulfonic acid radical, or are each, individually or together, an aromatic ring from the group consisting of phenyl, naphthyl, anthracenyl and phenanthrenyl, which may be unsubstituted or mono- or tetrasubstituted by A or Hal, or are each, individually or together, a heterocyclic aromatic ring from the group consisting of pyridyl, pyrazyl and bipyridyl, which may be unsubstituted or mono- to trisubstituted by A or Hal, or are each, individually or together, an aromatic hydroxy acid from the group consisting of aromatic hydroxycarboxylic acids and aromatic hydroxysulfonic acids, which may be unsubstituted or mono- to tetrasubstituted by A or Hal, and Hal is F, Cl or Br and A is alkyl having 1 to 6 carbon atoms, which may be mono- to trihalogenated.

Likewise suitable are alkali metal alkoxides of the general formula $$Li^+OR^-$$

in which

R is an aromatic or aliphatic carboxylic, dicarboxylic or sulfonic acid radical, or is an aromatic ring from the group consisting of phenyl, naphthyl, anthracenyl and phenanthrenyl, which may be unsubstituted or mono- or tetrasubstituted by A or Hal, or is a heterocyclic aromatic ring from the group consisting of pyridyl, pyrazyl and bipyridyl, which may be unsubstituted or mono- to trisubstituted by A or Hal, or is an aromatic hydroxy acid from the group consisting of aromatic hydroxycarboxylic acids and aromatic hydroxysulfonic acids, which may be unsubstituted or mono- to tetrasubstituted by A or Hal, and Hal is F, Cl or Br and A is alkyl having 1 to 6 carbon atoms, which may be mono- to trihalogenated.

Lithium complex salts of the formula

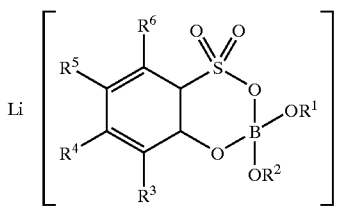

where
R$^1$ and R$^2$ are identical or different, are optionally bonded directly to one another via a single or double bond, and are each, individually or together, an aromatic ring from the group consisting of phenyl, naphthyl, anthracenyl and phenanthrenyl, which may be unsubstituted or mono- to hexasubstituted by alkyl (C$_1$ to C$_6$), alkoxy groups (C$_1$ to C$_6$) or halogen (F, Cl or Br),
or are each, individually or together, an aromatic heterocyclic ring from the group consisting of pyridyl, pyrazyl and pyrimidyl, which may be unsubstituted or mono- to tetrasubstituted by alkyl (C$_1$ to C$_6$), alkoxy groups (C$_1$ to C$_6$) or halogen (F, Cl or Br),
or are each, individually or together, an aromatic ring from the group consisting of hydroxybenzocarboxyl, hydroxynaphthalenecarboxyl, hydroxybenzosulfonyl and hydroxynaphthalenesulfonyl, which may be unsubstituted or mono- to tetrasubstituted by alkyl (C$_1$ to C$_6$), alkoxy groups (C$_1$ to C$_6$) or halogen (F, Cl or Br), R$^3$–R$^6$ may each, individually or in pairs and optionally bonded directly to one another via a single or double bond, have the following meanings:
1. alkyl (C$_1$ to C$_6$), alkoxy (C$_1$ to C$_6$) or halogen (F, Cl or Br)
2. an aromatic ring from the groups consisting of phenyl, naphthyl, anthracenyl and phenanthrenyl, which may be unsubstituted or mono- to hexasubstituted by alkyl (C$_1$ to C$_6$), alkoxy groups (C$_1$ to C$_6$) or halogen (F, Cl or Br), pyridyl, pyrazyl and pyrimidyl, which may be unsubstituted or mono- to tetrasubstituted by alkyl (C$_1$ to C$_6$), alkoxy groups (C$_1$ to C$_6$) or halogen (F, Cl or Br), which are prepared by the following process (DE 199 32 317):
a) chlorosulfonic acid is added to 3-, 4-, 5- or 6-substituted phenol in a suitable solvent,
b) the intermediate from a) is reacted with chlorotrimethylsilane, and the reaction mixture is filtered and subjected to fractional distillation,
c) the intermediate from b) is reacted with lithium tetramethoxyborate(1-) in a suitable solvent, and the end product is isolated therefrom, may also be present in the electrolyte.

The electrolytes may likewise comprise compounds of the following formula (DE 199 41 566):

where
Kt=N, P, As, Sb, S or Se,
A=N, P, P(O), O, S, S(O), SO$_2$, As, As(O), Sb or Sb(O),
R$^1$, R$^2$ and R$^3$ are identical or different
  and are H, halogen, substituted and/or unsubstituted alkyl C$_n$H$_{2n+1}$, substituted and/or unsubstituted alkenyl having 1–18 carbon atoms and one or more double bonds, substituted and/or unsubstituted alkynyl having 1–18 carbon atoms and one or more triple bonds, substituted and/or unsubstituted cycloalkyl C$_m$H$_{2m-1}$, mono- or polysubstituted and/or unsubstituted phenyl, or substituted and/or unsubstituted heteroaryl,
A can be included in R$^1$, R$^2$ and/or R$^3$ in various positions, Kt can be included in a cyclic or heterocyclic ring, the groups bonded to Kt may be identical or different,
where
n=1–18
m=3–7
k=0 or 1–6
l=1 or 2 in the case where x=1 and 1 in the case where x=0
x=0 or 1
y=1–4.

The process for the preparation of these compounds is characterized in that an alkali metal salt of the general formula $$D^+-N(CF_3)_2 \quad (II)$$

where D$^+$ is selected from the group consisting of the alkali metals, is reacted, in a polar organic solvent, with a salt of the general formula

where
Kt, A, R$^1$, R$^2$, R$^3$, k, l, x and y are as defined above, and $^-$E is F$^-$, Cl$^-$, Br$^-$, I$^-$, BF$_4^-$, ClO$_4^-$, AsF$_6^-$, SbF$_6^-$ or PF$_6^-$.

However, use can also be made of electrolytes comprising compounds of the general formula (DE 199 53 638)

where
X is H, F, Cl, C$_n$F$_{2n+1}$, C$_n$F$_{2n-1}$ or (SO$_2$)$_k$N(CR$^1$R$^2$R$^3$)$_2$,
Y is H, F or Cl
Z is H, F or Cl
R$^1$, R$^2$ and R$^3$ are H and/or alkyl, fluoroalkyl or cycloalkyl
m is 0–9 and, if X=H, m≠0
n is 1–9
k is 0 if m=0 and k=1 if m=1–9,
prepared by reacting partially or perfluorinated alkylsulfonyl fluorides with dimethylamine in organic solvents, and complex salts of the general formula (DE 199 51 804)

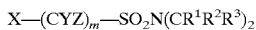

in which
x and y are 1, 2, 3, 4, 5 or 6
M$^{x+}$ is a metal ion
E is a Lewis acid selected from the group consisting of BR$^1$R$^2$R$^3$, AlR$^1$R$^2$R$^3$, PR$^1$R$^2$R$^3$R$^4$R$^5$, AsR$^1$R$^2$R$^3$R$^4$R$^5$ and VR$^1$R$^2$R$^3$R$^4$R$^5$,
R$^1$ to R$_5$ are identical or different, are optionally bonded directly to one another via a single or double bond, and each, individually or together, have the following meanings:
  a halogen (F, Cl or Br),
  an alkyl or alkoxy radical (C$_1$ to C$_8$), which can be partially or fully substituted by F, Cl or Br,
  an aromatic ring, optionally bonded via oxygen, from the group consisting of phenyl, naphthyl, anthracenyl and phenanthrenyl, which may be unsubstituted or mono- to hexasubstituted by alkyl ($C_1$ to $C_8$) or F, Cl or Br, an aromatic heterocyclic ring, optionally bonded via oxygen, from the group consisting of pyridyl, pyrazyl and pyrimidyl, which may be unsubstituted or mono- to tetrasubstituted by alkyl ($C_1$ to $C_8$) or F, Cl or Br, and Z is $OR^6$, $NR^6R^7$, $CR^6R^7R^8$, $OSO_2R^6$, $N(SO_2R^6)(SO_2R^7)$, $C(SO_2R^6)(SO_2R^7)(SO_2R^8)$ or $OCOR^6$, where $R^6$ to $R^8$ are identical or different, are optionally bonded directly to one another via a single or double bond and are each, individually or together, hydrogen or as defined for $R^1$ to $R^5$, prepared by reacting a corresponding boron or phosphorus Lewis acid/solvent adduct with a lithium or tetraalkylammonium imide, methanide or triflate.

They can also be employed in mixtures which comprise the borate salts (DE 199 59 722) of the general formula

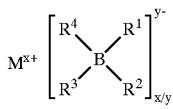

in which

M is a metal ion or a tetraalkylammonium ion, x and y are 1, 2, 3, 4, 5 or 6, $R^1$ to $R^4$ are identical or different and are alkoxy or carboxyl radicals ($C_1$–$C_8$), which are optionally bonded directly to one another via a single or double bond.

These electrolytes can be employed in electrochemical cells having negative electrodes made from common lithium intercalation and insertion compounds, but also with negative-electrode materials consisting of lithium mixed-oxide particles coated with one or more metal oxides or polymers.

Lithium mixed-oxide particles coated with one or more metal oxides are obtained by a process (DE 199 22 522) which is characterized in that the particles are suspended in an organic solvent, a solution of a hydrolysable metal compound and a hydrolysis solution are added to the suspension, and the coated particles are then filtered off, dried and optionally calcined. Lithium mixed-oxide particles coated with one or more polymers are obtained by a process (DE 199 46 066) which is characterized in that particles are suspended in a solution comprising polymers selected from the group consisting of polyimides, polyanilines, polypyrroles, polythiophenes, polyacetylenes, polyacrylonitriles, carbonized polyacrylonitriles, poly-p-phenylenes, polyphenylenevinylenes, polyquinolines, polyquin-oxalines, polyphthalocyanine-siloxanes, polyvinylidene fluorides, polytetrafluoroethylenes, polyethyl methacrylates, polymethyl methacrylates, polyamides, copolymers with vinyl ethers, cellulose, polyfluoroethylenes, polyvinyl alcohols and polyvinylpyridines, and derivatives thereof, and the coated particles are then filtered off, dried, and optionally calcined.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above, are hereby incorporated by reference.

This application claims priority under 35 USC Section 119 to German Patent Application 199 19 346.0, filed Apr. 28, 1999, which application is expressly incorporated herein by reference.

EXAMPLES

Example 1

Purification of tris(perfluoroalkanesulfonyl)methanides

1st Step

Lithium or cesium tris(trifluoromethanesulfonyl)methanide (purity 97.5–99.5%) was introduced in portions into freshly distilled sulfuric acid, and the mixture was stirred at room temperature for ten minutes. The round-bottom flask was subsequently connected to a distillation apparatus with isothermal column which had been baked out under an argon atmosphere, and the mixture was subjected to fractional rectification at a pressure of 10 Pa. The distillation bridge was provided with a heating tape from the column head in order to obtain a constant temperature above the respective melting point in the bridge. The ground-glass joints were provided with Teflon sleeves. The same procedure was used for other derivatives of tris (perfluoroalkanesulfonyl)methanes.

Table 1 shows the various methanides and the yields of free acid.

TABLE 1

| Compound | Amount [g] | Amount [mol] | Boiling point of the acid [° C.] [10 Pa] | Acid yield [%] |
|---|---|---|---|---|
| $Li^+$ $C(CF_3SO_2)_3^-$ | 17 | 0.04 | 132–136 | 72 |
| $Cs^+$ $C(CF_3SO_2)_3^-$ | 27 | 0.05 | 135–136 | 68 |
| $Li^+$ $C(CF_3SO_2)_3^-$ | 68 | 0.16 | 135–137 | 87 |
| $Li^+$ $C(CF_3SO_2)_2(C_4F_9SO_2)^-$ | 19 | 0.03 | 143–145 | 43 |
| $HC(CF_3SO_2)_3$ content 89% | 323 | 0.67 | 135–137 | 95 |

2nd Step

A portion of the pure fraction of $HC(CF_3SO_2)_3$ from step 1 was mixed with phosphorus pentoxide, and the flask containing the mixture was connected to the distillation apparatus, which had been baked out under an argon atmosphere. The mixture was melted, stirred for one hour at 90° C. under atmospheric pressure and subjected to fractional rectification under reduced pressure.

| | |
|---|---|
| Weighed-out amount of tris(trifluoromethanesulfonyl)methane | 86 g |
| Added amount of phosphorus pentoxide | 4 g |
| Pressure | 10 Pa |
| 1st fraction 135–137° C. | 11 g |
| 2nd fraction 138° C. | 62.4 g |

3rd Step 62.4 g (0.151 mol) of tris(trifluoromethanesulfonyl)methane were dissolved in 100 ml of diethyl carbonate under a dry inert-gas atmosphere and reacted with 1.215 g lithium hydride. When the addition was complete, the electrolyte was stirred for 30 minutes, and the excess lithium hydride was subsequently separated off via a filter.

4th Step

The volume of the electrolyte was reduced to 30 ml at room temperature and a pressure of $10^{-5}$ Pa.

5th Step

The colorless electrolyte, which was now of high viscosity, was diluted with 120 ml of solvent mixture (ethylene carbonate:dimethyl carbonate 1:1) to give 150 ml of a 1 molar electrolyte.

A 500 μl NMR sample of the finished electrolyte was mixed with 250 μl of $CD_3COCD_3$ and measured. Bruker Advance DRX 500 NMR spectrometer:

470.53 MHz, 35° C.

$^{19}$F-NMR spectrum:

d=−76.488; s; $Li^+C(CF_3SO_2)_3^-$

Even at the maximum amplification of the spectrum, no $^{19}$F-containing impurities were detected.

A water content of 28 ppm was found.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process comprising:

reacting a starting methanide of formula (I)

$$MC(SO_2(C_xF_{2x+1}))_3 \qquad (I)$$

in which x is 1, 2, 3, 4, 5, 6, 7 or 8, and

M is H, Li, Na, K, Rb, Cs, $Mg_{1/2}$, $Ca_{1/2}$, $Sr_{1/2}$ or $Ba_{1/2}$, with concentrated sulfuric acid to form a free acid of the methanide, subjecting the free acid of the methanide to fractional rectification, reacting the fractionally rectified free acid of the methanide with phosphorus pentoxide to form a reaction product, subjecting the reaction product to fractional rectification, and reacting the fractionally rectified reaction product with metallic Li, Na, K, Rb, Cs, Mg, Ca, Sr, Ba, chlorides or hydrides thereof, or alkyllithium, in an aprotic solvent to form a corresponding high purity metal methanide of the formula (I) in a solution.

2. A process according to claim 1, further comprising removing from 1/3 to 3/4 of the solvent by distillation after the metal methanide of the formula (I) is formed.

3. A process according to claim 2, wherein about 2/3 of the solvent is removed by distillation.

4. A process according to claim 3, further comprising diluting the solution with a solvent.

5. A process according to claim 1, wherein the solvent comprises a solvent suitable for use as an electrolyte solvent.

6. A process according claim 1, wherein the starting methanide of the formula (I) has a purity of from 90% to 99.5%.

7. A process according to claim 1, wherein the high-purity methanide has a purity of greater than 99.5%.

8. A process according to claim 1, wherein the high purity methanide has a purity of from 99.6% to 99.9%.

9. A process according to claim 1, wherein the high purity methanide has a water content of from 5 to 30 ppm.

10. A process according to claim 1, wherein the high purity methanide has a water content of from 10 to 20 ppm.

11. A process as claimed in claim 1, wherein reacting the fractionally rectified free acid of the methanide with phosphorus pentoxide to form a reaction product occurs at or above the melting point.

12. A process as claimed in claim 2, wherein reacting the fractionally rectified free acid of the methanide with phosphorus pentoxide to form a reaction product occurs at or above the melting point.

13. A process for the preparation of high-purity methanides as claimed in claim 1, wherein the starting methanide is of the formula (II)

$$LiC(SO_2(C_xF_{2x+1}))_3 \qquad (II).$$

14. A process according to claim 13, wherein the fractionally rectified reaction product is reacted with lithium hydride in dimethyl carbonate.

15. A process for the preparation of high-purity methanides of the formula (I)

$$MC(SO_2(C_xF_{2x+1}))_3 \qquad (I)$$

in which x is 1, 2, 3, 4, 5, 6, 7 or 8, and

M is Li, Na, K, Rb, Cs, $Mg_{1/2}$, $Ca_{1/2}$, $Sr_{1/2}$ or $Ba_{1/2}$, comprising (i) reacting a starting methanide of formula (I) with concentrated sulfuric acid to form a free acid of the methanide, and fractional rectification of the resultant free acid of the methanide, (ii) reacting the product of formula I in which M=H obtained in i) with phosphorus pentoxide, followed by fractional rectification, and (iii) taking up the product of (ii) in an aprotic organic solvent, and reacting the product of (ii) with metallic Li, Na, K, Rb, Cs, Mg, Ca, Sr, Ba, chlorides or hydrides thereof, or alkyllithium, in an aprotic. solvent to form a corresponding high purity metal methanide of the formula (I), and optionally, removal of any excess reagent.

16. A process for the preparation of a methanide of formula (I)

$$MC(SO_2(C_xF_{2x+1}))_3 \qquad (I)$$

in which x is 1, 2, 3, 4, 5, 6, 7 or 8, and

M is Li, Na, K, Rb, Cs, $Mg_2$, $Ca_{1/2}$, $Sr_{1/2}$ or $Ba_{1/2}$,

Comprising reacting a fractionally rectified free acid of the methanide with phosphorous pentoxide, followed by reaction with metallic Li, Na, K, Rb, Cs, Mg, Ca, Sr, Ba, chlorides or hydrides thereof, or alkyllithium, in an aprotic solvent to form a corresponding high purity metal methanide of the formula (I) in a solution.

17. A process for the preparation of a methanide of formula (I)

$$MC(SO_2(C_xF_{2x+1}))_3 \qquad (I)$$

in which x is 1, 2, 3, 4, 5, 6, 7 or 8, and

M is Li, Na, K, Rb, Cs, $Mg_{1/2}$, $Ca_{1/2}$, $Sr_{1/2}$ or $Ba_{1/2}$, comprising reacting the fractionally rectified reaction product of a methanide free acid and phosphorous pentoxide with metallic Li, Na, K, Rb, Cs, Mg, Ca, Sr, Ba, chlorides or hydrides thereof, or alkyllithium, in an aprotic solvent to form a corresponding high purity metal methanide of the formula (I) in a solution.

18. In a process for the preparation of a methanide of formula (I)

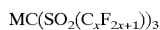  (I)

in which
x is 1, 2, 3, 4, 5, 6, 7 or 8, and
M is Li, Na, K, Rb, Cs, $Mg_{1/2}$, $Ca_{1/2}$, $Sr_{1/2}$ or $Ba_{1/2}$,
the step comprising reacting a starting methanide of formula (1) with concentrated sulfuric acid to form a free acid of the methanide.

19. In a process for the preparation of a methanide of formula (I)

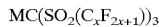  (I)

in which
x is 1, 2, 3, 4, 5, 6, 7 or 8, and
M is Li, Na, K, Rb, Cs, $Mg_{1/2}$, $Ca_{1/2}$, $Sr_{1/2}$ or $Ba_{1/2}$,
the step comprising reacting a free methanide acid with metallic Li, Na, K, Rb, Cs, Mg, Ca, Sr, Ba, chlorides or hydrides thereof, or alkyllithium, in an aprotic solvent to form a corresponding metal methanide of the formula (I) in a solution.

20. A process according to claim 1, further comprising introducing a high-purity methanide of formula I into an electrochemical cell.

* * * * *